United States Patent
Ueno et al.

(10) Patent No.: US 9,985,217 B2
(45) Date of Patent: May 29, 2018

(54) MATERIAL FOR ORGANIC ELECTROLUMINESCENT DEVICE AND ORGANIC ELECTROLUMINESCENT DEVICE INCLUDING THE SAME

(71) Applicant: SAMSUNG DISPLAY CO., LTD., Yongin-si, Gyeonggi-do (KR)

(72) Inventors: Masatsugu Ueno, Yokohama (JP); Junta Fuchiwaki, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 181 days.

(21) Appl. No.: 14/981,707

(22) Filed: Dec. 28, 2015

(65) Prior Publication Data

US 2016/0190468 A1   Jun. 30, 2016

(30) Foreign Application Priority Data

Dec. 26, 2014   (JP) .................. 2014-265301

(51) Int. Cl.
*H01L 51/50*  (2006.01)
*H01L 51/00*  (2006.01)
(Continued)

(52) U.S. Cl.
CPC ........ *H01L 51/0061* (2013.01); *C07D 209/80* (2013.01); *C07D 209/86* (2013.01);
(Continued)

(58) Field of Classification Search
None
See application file for complete search history.

(56) References Cited

U.S. PATENT DOCUMENTS

2007/0231503 A1   10/2007   Hwang et al.
2014/0296519 A1*  10/2014   Matsumoto .......... C07D 209/86
                                                        544/212

(Continued)

FOREIGN PATENT DOCUMENTS

JP                4103492 B2        6/2008
JP           2012-049518 A          3/2012
(Continued)

OTHER PUBLICATIONS

Abstract for Japanese Pub. No. JP 2004071500 A, dated Mar. 4, 2004, for corresponding JP 4103492 B2, 2 pages.
(Continued)

*Primary Examiner* — Gregory D Clark
(74) *Attorney, Agent, or Firm* — Lewis Roca Rothgerber Christie LLP

(57) ABSTRACT

A material for an organic electroluminescent device and an organic electroluminescent device including the same, according to one or more embodiments of the present disclosure, include an amine derivative represented by Formula 1. When the amine derivative represented by Formula 1 is included in the emission layer, the emission efficiency of the organic electroluminescent device may be improved.

Formula 1

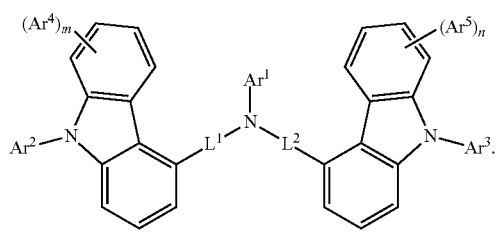

20 Claims, 1 Drawing Sheet

(51) Int. Cl.
  *C07D 209/86* (2006.01)
  *C07D 209/80* (2006.01)
(52) U.S. Cl.
  CPC ...... *H01L 51/0059* (2013.01); *H01L 51/0072* (2013.01); *H01L 51/5056* (2013.01)

(56) References Cited

FOREIGN PATENT DOCUMENTS

| KR | 10-1395080 B1 | 5/2014 |
| WO | WO 2010/110533 A2 | 9/2010 |
| WO | WO 2011/125680 A1 | 10/2011 |
| WO | WO 2012/091471 A2 | 7/2012 |

OTHER PUBLICATIONS

Abstract for Korean Pub. No. KR 20130113263 A, dated Oct. 15, 2013, for corresponding KR 10-1395080 B1, 1 page.

* cited by examiner

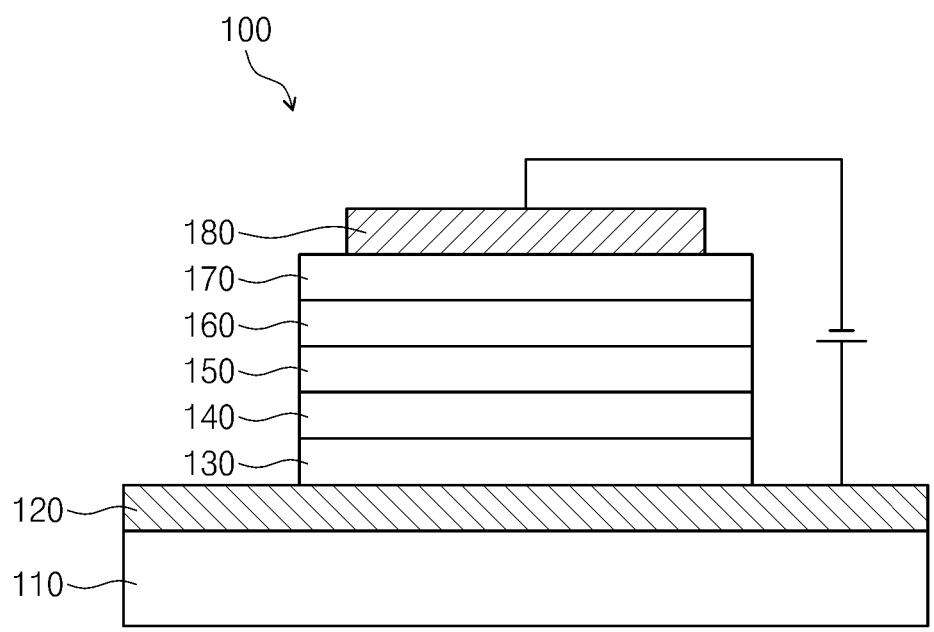

MATERIAL FOR ORGANIC ELECTROLUMINESCENT DEVICE AND ORGANIC ELECTROLUMINESCENT DEVICE INCLUDING THE SAME

CROSS-REFERENCE TO RELATED APPLICATION

This patent application claims priority to and the benefit of Japanese Patent Application No. 2014-265301, filed on Dec. 26, 2014, the entire content of which is hereby incorporated by reference.

BACKGROUND

1. Field

One or more aspects of embodiments of the present disclosure relate to a material for an organic electroluminescent device, and an organic electroluminescent device including the same.

2. Description of the Related Art

Organic electroluminescent displays are being actively developed, and research is being conducted on organic electroluminescent devices that are so-called self-luminescent devices used in organic electroluminescent displays.

An example organic electroluminescent device has a structure including an anode, a hole transport layer on the anode, an emission layer on the hole transport layer, an electron transport layer on the emission layer, and a cathode on the electron transport layer.

In such an organic electroluminescent device, holes and electrons injected from the anode and the cathode recombine in the emission layer to generate excitons, and light is emitted when the generated excitons transition back to the ground state. The use of an amine derivative including a carbazolyl group as a hole transport material or hole injection material in a hole transport layer or a hole injection layer has been investigated.

SUMMARY

However, organic electroluminescent devices using an amine derivative including a carbazolyl group as a hole transport material have not shown satisfactory values of emission efficiency.

One or more aspects of embodiments of the present disclosure are directed toward a novel and improved material for an organic electroluminescent device that may improve the emission efficiency of an organic electroluminescent device, and an organic electroluminescent device including the same.

One or more embodiments of the present disclosure provide a material for an organic electroluminescent device including an amine derivative, as represented by Formula 1:

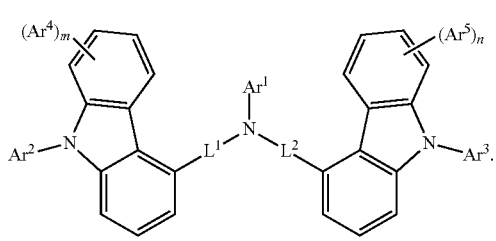

Formula 1

In Formula 1, $Ar^1$ to $Ar^3$ may each independently be selected from a substituted or unsubstituted aryl group having 6 to 50 carbon atoms for forming a ring, and a substituted or unsubstituted heteroaryl group having 5 to 50 carbon atoms for forming a ring, $Ar^4$ and $Ar^5$ may each independently be selected from hydrogen, deuterium, a halogen atom, a substituted or unsubstituted alkyl group having 1 to 20 carbon atoms and having a linear or branched shape, a substituted or unsubstituted aryl group having 6 to 50 carbon atoms for forming a ring, a substituted or unsubstituted heteroaryl group having 5 to 50 carbon atoms for forming a ring, and an aryl group or a heteroaryl group formed via cyclocondensation of adjacent optional substituents, $L^1$ and $L^2$ may each independently be selected from a direct linkage, a substituted or unsubstituted arylene group having 6 to 18 carbon atoms for forming a ring, and a substituted or unsubstituted heteroarylene group having 5 to 15 carbon atoms for forming a ring, and n and m may each independently be an integer selected from 0 to 4.

According to one or more aspects of embodiments of the present disclosure, the emission efficiency of the organic electroluminescent device may be improved.

In one or more embodiments, $Ar^1$ to $Ar^3$ may each independently be selected from a substituted or unsubstituted aryl group having 6 to 18 carbon atoms for forming a ring, and a substituted or unsubstituted heteroaryl group having 5 to 18 carbon atoms for forming a ring.

According to one or more aspects of embodiments of the present disclosure, the emission efficiency of the organic electroluminescent device may be improved.

In one or more embodiments, $Ar^1$ to $Ar^3$ may each independently be selected from a substituted or unsubstituted phenyl group and a substituted or unsubstituted biphenyl group.

According to one or more aspects of embodiments of the present disclosure, the emission efficiency of the organic electroluminescent device may be improved.

In one or more embodiments, $L^1$ and $L^2$ may each independently be a phenylene group.

According to one or more aspects of embodiments of the present disclosure, the emission efficiency of the organic electroluminescent device may be improved.

In one or more embodiments of the present disclosure, an organic electroluminescent device includes an anode, a hole injection layer on the anode, a hole transport layer on the hole injection layer, and an emission layer on the hole transport layer, the emission layer including a material for an organic electroluminescent device represented by Formula 1:

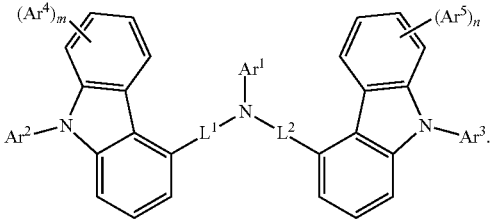

Formula 1

In Formula 1, $Ar^1$ to $Ar^3$ may each independently be selected from a substituted or unsubstituted aryl group having 6 to 50 carbon atoms for forming a ring, and a substituted or unsubstituted heteroaryl group having 5 to 50 carbon atoms for forming a ring, $Ar^4$ and $Ar^5$ may each independently be selected from hydrogen, deuterium, a halogen atom, a substituted or unsubstituted alkyl group having 1 to 20 carbon atoms, a substituted or unsubstituted aryl group having 6 to 50 carbon atoms for forming a ring, a substituted or unsubstituted heteroaryl group having 5 to 50 carbon atoms for forming a ring, and an aryl group or a heteroaryl group formed via cyclocondensation of adjacent optional substituents, $L^1$ and $L^2$ may each independently be selected from a direct linkage, a substituted or unsubstituted arylene group having 6 to 18 carbon atoms for forming a ring, and a substituted or unsubstituted heteroarylene group having 5 to 15 carbon atoms for forming a ring, and n and m may each independently be an integer selected from 0 to 4.

According to one or more aspects of embodiments of the present disclosure, the emission efficiency of the organic electroluminescent device may be improved.

In one or more embodiments, at least one layer selected from the hole injection layer and the hole transport layer may include the material for an organic electroluminescent device represented by Formula 1.

According to one or more aspects of embodiments of the present disclosure, the emission efficiency of the organic electroluminescent device may be improved.

In one or more embodiments, the emission layer may include a blue luminescent material or a green luminescent material.

According to one or more aspects of embodiments of the present disclosure, the emission efficiency of the organic electroluminescent device may be improved.

BRIEF DESCRIPTION OF THE DRAWINGS

The accompanying drawing is included to enhance further understanding of the present disclosure, and is incorporated in and constitutes a part of this specification. The drawing illustrates example embodiments of the present disclosure and, together with the description, serves to explain principles of the present disclosure.

The drawing is a cross-sectional view showing the schematic configuration of an organic electroluminescent device according to one or more embodiments of the present disclosure.

DETAILED DESCRIPTION

Example embodiments of the present disclosure will be described below in more detail with reference to the accompanying drawing. As those skilled in the art would realize, the described embodiments may be modified in one or more different ways, all without departing from the spirit or scope of the present disclosure. In the description and drawing, like reference numerals refer to like elements throughout and duplicative descriptions thereof will not be provided. The thickness of layers, films, panels, regions, etc., may be exaggerated in the drawings for clarity. It will be understood that when an element such as a layer, film, region, or substrate is referred to as being "on" another element, it can be directly on the other element or intervening elements may also be present. In contrast, when an element is referred to as being "directly on" another element, no intervening elements are present.

1. Structure of the Material for an Organic Electroluminescent Device

First, the structure of the material for an organic electroluminescent device according to an embodiment of the present disclosure will be explained. The material for an organic electroluminescent device according to one or more embodiments of the present disclosure may include an amine derivative, as represented by the following Formula 1:

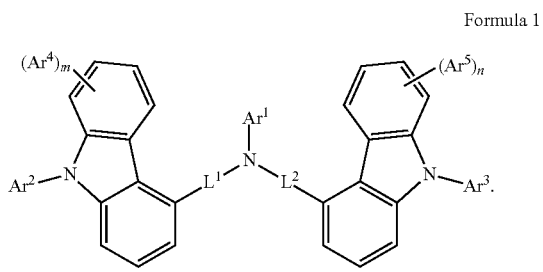

Formula 1

The amine derivative represented by Formula 1 may include two carbazolyl groups, and the nitrogen atom of an amine may be combined (e.g., coupled) with the carbon atom of each carbazolyl group at position 4 via $L^1$ or $L^2$.

In the amine derivative, two carbazolyl groups may be combined with the nitrogen atom of the amine at the same substitution positions via $L^1$ and $L^2$, and the molecular structure around the nitrogen atom of the amine may be highly symmetric. Due to these structural characteristics, the emission efficiency of an organic electroluminescent device containing this molecule may be improved.

In Formula 1, $Ar^1$ to $Ar^3$ may each independently be selected from a substituted or unsubstituted aryl group having 6 to 50 carbon atoms for forming a ring, and a substituted or unsubstituted heteroaryl group having 5 to 50 carbon atoms for forming a ring. As used herein, "atoms for forming a ring" may refer to "ring-forming atoms".

$Ar^1$ to $Ar^3$ may each independently be selected from a substituted or unsubstituted aryl group having 6 to 18 carbon atoms for forming a ring, and a substituted or unsubstituted heteroaryl group having 5 to 18 carbon atoms for forming a ring. In some embodiments, $Ar^1$ to $Ar^3$ may each independently be selected from a substituted or unsubstituted phenyl group or a substituted or unsubstituted biphenyl group.

In Formula 1, $Ar^1$ to $Ar^3$ may each independently be selected from a substituted or unsubstituted phenyl group, a substituted or unsubstituted biphenyl group, a substituted or unsubstituted terphenyl group, a substituted or unsubstituted naphthyl group, a substituted or unsubstituted anthryl group, a substituted or unsubstituted phenanthrenyl group, a substituted or unsubstituted fluorenyl group, a substituted or unsubstituted indenyl group, a substituted or unsubstituted pyrenyl group, a substituted or unsubstituted fluoranthenyl group, a substituted or unsubstituted triphenylenyl group, a substituted or unsubstituted perylenyl group, a substituted or unsubstituted naphthylphenyl group, and a substituted or unsubstituted biphenylenyl group.

In Formula 1, $Ar^1$ to $Ar^3$ may each independently be selected from a substituted or unsubstituted pyridyl group, a substituted or unsubstituted quinolyl group, a substituted or unsubstituted isoquinolyl group, a substituted or unsubstituted indolyl group, a substituted or unsubstituted benzoxazolyl group, a substituted or unsubstituted benzothiazolyl group, a substituted or unsubstituted quinoxalyl group, a substituted or unsubstituted benzoimidazolyl group, a substituted or unsubstituted indazolyl group, a substituted or unsubstituted benzofuranyl group, a substituted or unsubstituted isobenzofuranyl group, a substituted or unsubstituted dibenzofuranyl group, a substituted or unsubstituted phenoxazinyl group, a substituted or unsubstituted benzothiophenyl group, and a substituted or unsubstituted dibenzothiophenyl group.

In Formula 1, the aryl group and/or heteroaryl substituent groups forming $Ar^1$ to $Ar^3$ may be replaced with substituents selected from an alkyl group (for example, a methyl group, an ethyl group, etc.), an alkenyl group (for example, a vinyl group, etc.), a halogen atom (for example, a fluorine, a chlorine, etc.), a silyl group (for example, a trimethylsilyl group, etc.), a cyano group, an alkoxy group (for example, a methoxy group, a butoxy group, etc.), a nitro group, a hydroxyl group, a thiol group, etc. In some embodiments, the substituent may be a functional group other than a vinyl group, an indolyl group, and a triphenylenyl group, in consideration of thermal stability. The substituents may be additionally substituted with the same substituents.

In Formula 1, $Ar^4$ and $Ar^5$ may each independently be selected from hydrogen, deuterium, a halogen atom, an alkyl group having 1 to 20 carbon atoms and a linear or branched shape, a substituted or unsubstituted aryl group having 6 to 50 carbon atoms for forming a ring, and a substituted or unsubstituted heteroaryl group having 5 to 50 carbon atoms for forming a ring. Adjacent $Ar^4$ or adjacent $Ar^5$ substituents may combine (e.g., couple or undergo cyclocondensation) with each other to form a ring.

The halogen atom may be selected from fluorine, chlorine, bromine and iodine.

Referring to $Ar^4$ and $Ar^5$ of Formula 1, the alkyl group having 1 to 20 carbon atoms may be selected from a linear alkyl group (for example, a methyl group, an ethyl group, a propyl group, a butyl group, an octyl group, a decyl group, a pentadecyl group, etc.) and a branched alkyl group (for example, a t-butyl group, etc.).

Referring to $Ar^4$ and $Ar^5$ of Formula 1, the substituted or unsubstituted aryl group having 6 to 50 carbon atoms for forming a ring and the substituted or unsubstituted heteroaryl group having 5 to 50 carbon atoms for forming a ring may be selected from the substituted or unsubstituted aryl groups and heteroaryl groups used for $Ar^1$ to $Ar^3$. The substituents of the aryl group and the heteroaryl group may be the same as the substituents of the aryl group and the heteroaryl group used for $Ar^1$ to $Ar^3$.

In Formula 1, $L^1$ and $L^2$ may be selected from a direct linkage, a substituted or unsubstituted arylene group having 6 to 18 carbon atoms for forming a ring, and a substituted or unsubstituted heteroarylene group having 5 to 15 carbon atoms for forming a ring. As used herein, "direct linkage" may refer to a bond such as a single bond. In some embodiments, $L^1$ and $L^2$ may be a phenylene group. In Formula 1, the direct linkage of $L^1$ and/or $L^2$ may refer to the direct combination (e.g., coupling) of the nitrogen atom of the amine with the respective carbazolyl group.

The aryl group and the heteroaryl groups of $Ar^1$ to $Ar^3$ may each independently be selected from divalent groups having substantially the same structures as the substituted or unsubstituted arylene group having 6 to 18 carbon atoms for forming a ring and the substituted or unsubstituted heteroarylene group having 5 to 15 carbon atoms for forming a ring, obtained by removing one more hydrogen atom from the aryl group having 6 to 18 carbon atoms for forming a ring or the heteroaryl group having 5 to 15 carbon atoms for forming a ring.

n and m may each independently be an integer selected from 0 to 4. When n and/or m are greater than or equal to 2, a plurality of $Ar^4$ may be the same or different from each other. A plurality of $Ar^5$ may be the same or different from each other.

In one or more embodiments, the amine derivative represented by Formula 1 may improve the emission efficiency of the organic electroluminescent device when a blue luminescent material or a green luminescent material is included in an emission layer.

The material for an organic electroluminescent device including the amine derivative represented by Formula 1 may be included in at least one layer between the emission layer and the anode of the organic electroluminescent device. In one or more embodiments, the material for an organic electroluminescent device including the amine derivative represented by Formula 1 may be included in the hole transport layer or the hole injection layer of the organic electroluminescent device. However, the use of the amine derivative represented by Formula 1 is not limited to the above-mentioned layers in the organic electroluminescent device. For example, the amine derivative represented by Formula 1 may be included in one or more of any organic layers formed between the anode and the cathode of the organic electroluminescent device, and in some embodiments, in an emission layer.

The material for an organic electroluminescent device having the above-described configuration may improve the emission efficiency of an organic electroluminescent device as described in the following example embodiments. Hereinafter, examples of the amine derivative included in the material for an organic electroluminescent device will be illustrated in Compounds 1 to 18. (Compounds 1 to 8 are collectively denoted as Formula 2, Compounds 9 to 16 are collectively denoted as Formula 3, and Compounds 17 to 18 are collectively denoted as Formula 4). However, the amine derivative according to an embodiment of the present disclosure is not limited to the following compounds:

Formula 2

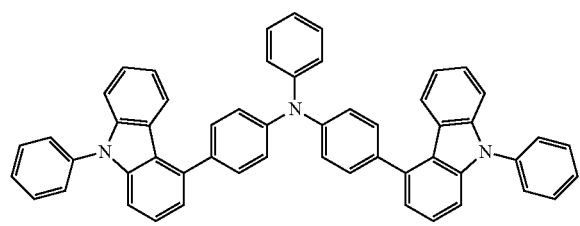

1

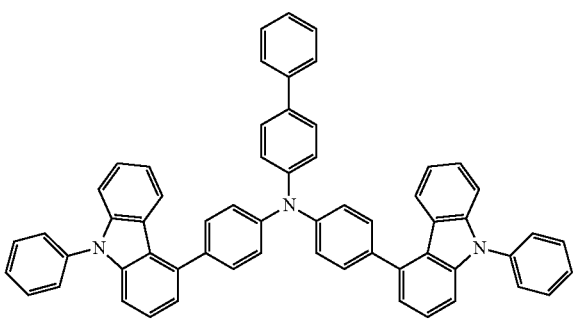

2

-continued
3
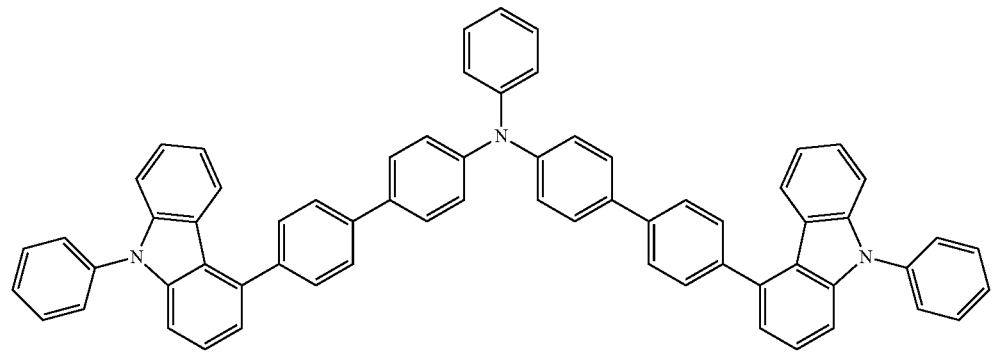
4
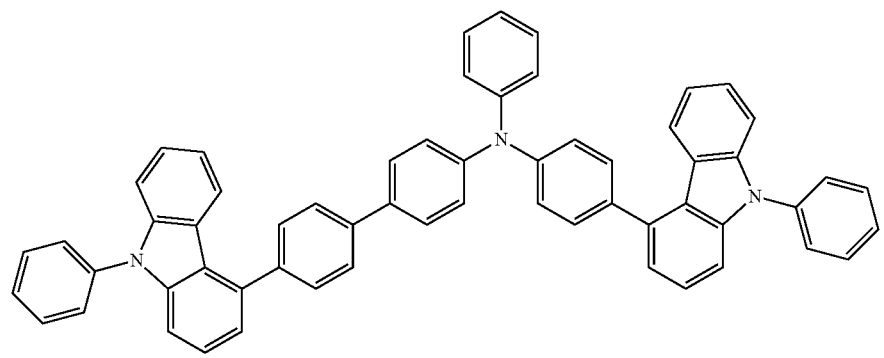
5
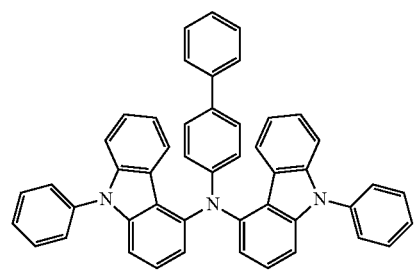
6
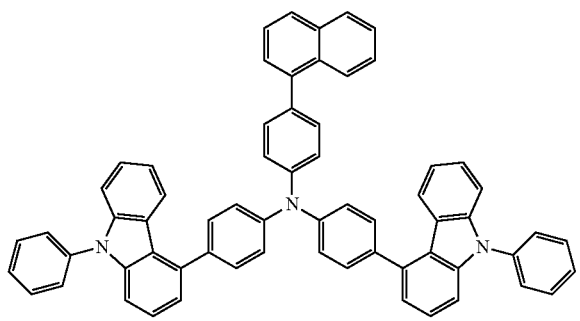
7
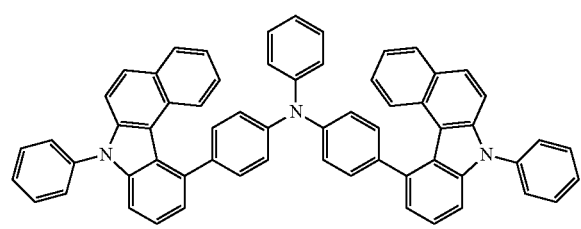
8
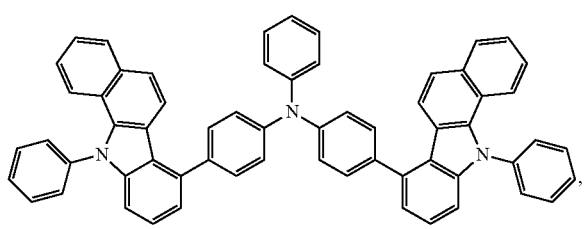

Formula 3
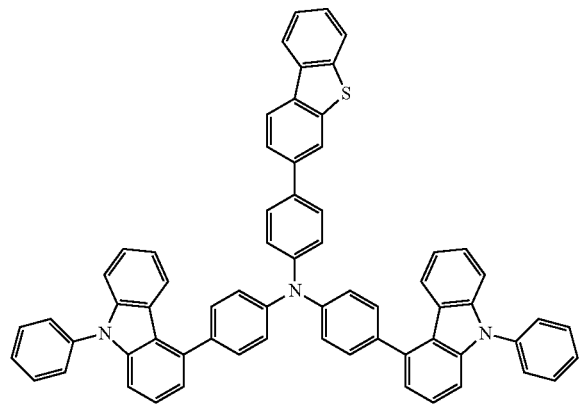
9
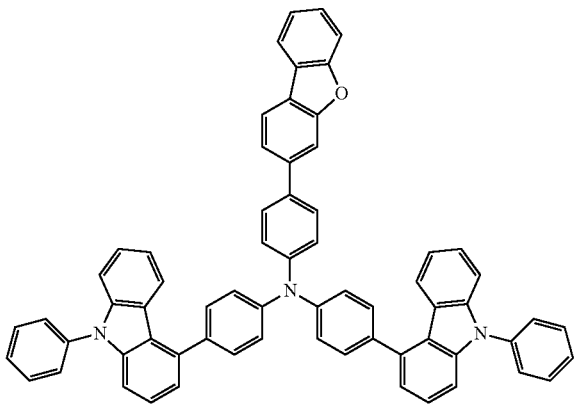
10
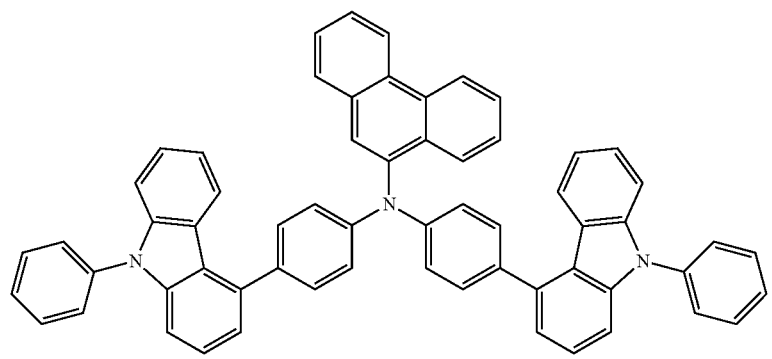
11
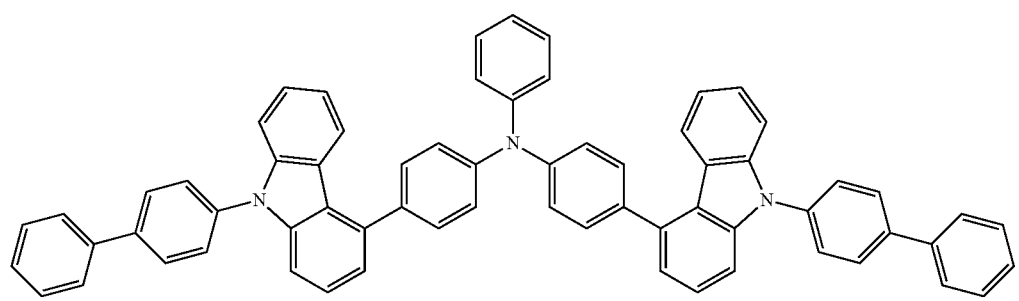
12
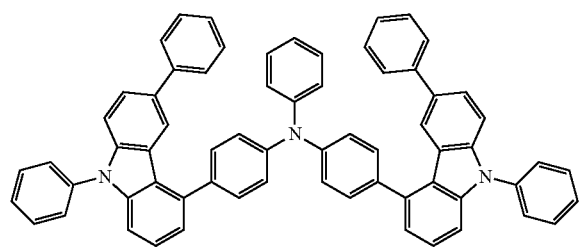
13
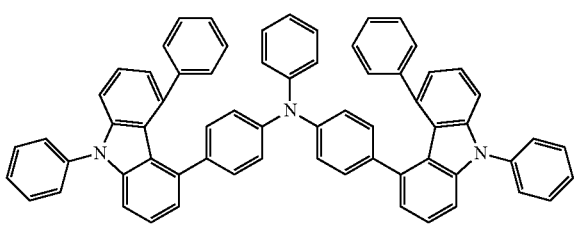
14

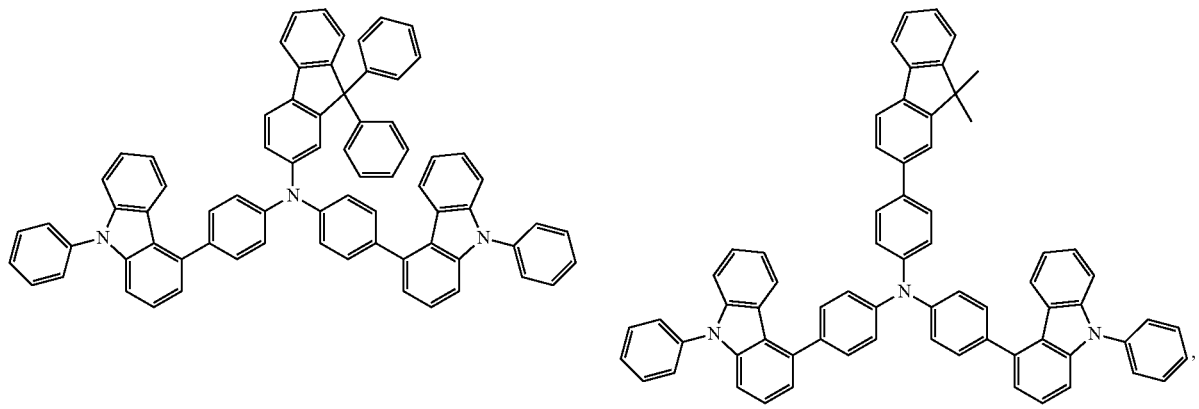

Formula 4

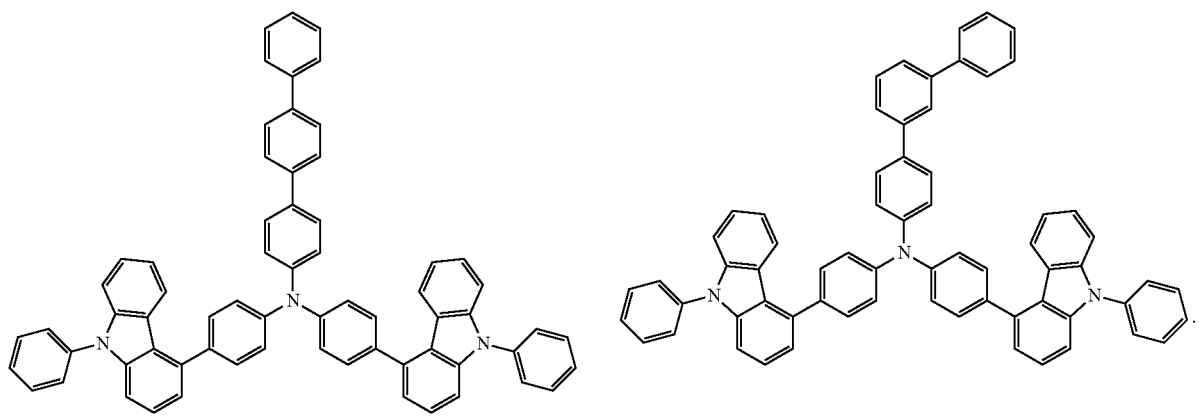

2. Organic Electroluminescent Device Including the Material for an Organic Device Referring to FIG. 1, an organic electroluminescent device including a material for an organic electroluminescent device according to an embodiment of the present disclosure will be described. FIG. 1 is a schematic cross-sectional view of an organic electroluminescent device according to an embodiment of the present disclosure.

As shown in FIG. 1, an organic electroluminescent device 100 according to an embodiment of the present disclosure may include a substrate 110, a first electrode 120 on the substrate 110, a hole injection layer 130 on the first electrode 120, a hole transport layer 140 on the hole injection layer 130, an emission layer 150 on the hole transport layer 140, an electron transport layer 160 on the emission layer 150, an electron injection layer 170 on the electron transport layer 160 and a second electrode 180 on the electron injection layer 170.

The material for an organic electroluminescent device according to an embodiment of the present disclosure may be included in at least one layer selected from the hole transport layer and the emission layer. The material for the organic electroluminescent device may be included in both of the layers. For example. the material for the organic electroluminescent device may be included in the hole transport layer 140.

Each of the organic thin layers between the first electrode 120 and the second electrode 180 of the organic electroluminescent device may be formed using one or more suitable methods such as an evaporation method.

The substrate 110 may be any suitable substrate used in an organic electroluminescent device. For example, the substrate 110 may be a glass substrate, a semiconductor substrate, and/or a transparent plastic substrate.

The first electrode 120 may be an anode and may be formed on the substrate 110 using any suitable method such as evaporation, sputtering, etc. In one or more embodiments, the first electrode 120 may be formed as a transmission type (e.g., transmission) electrode using a metal, an alloy, a conductive compound, etc. having a high work function. In one or more embodiments, the first electrode 120 may be formed using transparent and highly conductive indium tin oxide ($In_2O_3$—$SnO_2$: ITO), indium zinc oxide ($In_2O_3$—ZnO: IZO), tin oxide ($SnO_2$), zinc oxide (ZnO), etc. In one or more embodiments, the first electrode 120 may be formed as a reflection type (e.g., reflection) electrode using magnesium (Mg), aluminum (Al), etc.

The hole injection layer 130 may be formed on the first electrode 120. The hole injection layer 130 may facilitate easy injection of holes from the first electrode 120 and in some embodiments, may be formed on the first electrode 120 to a thickness of about 10 nm to about 150 nm. The hole injection layer 130 may be formed using any suitable material. Non-limiting examples of this material may include triphenylamine-containing polyether ketone (TPA-PEK), 4-isopropyl-4'-methyldiphenyliodoniumtetrakis(pentaflorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methyl phenylamino)triphenylamine (m-MTDATA), N,N'-di(1-naphthyl)-N,N'-diphenylbenzidine (NPB), 4,4',4"-tris{N,N-diamino}triphenylamine (TDATA), 4,4',4"-tris(N,N-2-naphthylphenylamino)triphenylamine (2-TNATA), polyaniline/dodecylbenzenesulfonic acid (Pani/DBSA), poly(3,4-ethylenedioxythiophene)/poly(4-styrenesulfonate) (PEDOT/PSS), polyaniline/camphorsulfonic acid (Pani/CSA), polyaniline/poly(4-styrenesulfonate (PANI/PSS), etc.

The hole transport layer 140 may be formed on the hole injection layer 130. The hole transport layer 140 may be formed by stacking a plurality of layers. The hole transport layer 140 may include a hole transport material having hole transporting function and in some embodiments, may be formed on the hole injection layer 130 to a thickness of about 10 nm to about 150 nm. The hole transport layer 140 may be formed using the material for an organic electroluminescent device according to one or more embodiments. In the case that the material for an organic electroluminescent device according to an embodiment of the present disclosure is used as the host material of the emission layer 150, the hole transport layer 140 may be formed using any suitable hole transport material. Non-limiting examples of the suitable hole transport material may include 1,1-bis[(di-4-tolylamino)phenyl]cyclohexane (TAPC), a carbazole derivative such as N-phenyl carbazole and polyvinyl carbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphthyl)-N,N'-diphenylbenzidine (NPB), etc.

The emission layer 150 may be formed on the hole transport layer 140. The emission layer 150 may emit light via fluorescence, phosphorescence, etc. and in some embodiments, may be formed to a thickness of about 10 nm to about 60 nm. The material of the emission layer 150 may be any suitable luminescent material, without limitation, and may be selected from fluoranthene derivatives, pyrene derivatives, arylacetylene derivatives, fluorene derivatives, perylene derivatives, chrysene derivatives, etc. In some embodiments, a pyrene derivative, a perylene derivative and an anthracene derivative may be used. In one or more embodiments, an anthracene derivative represented by the following Formula 5 may be used as the material of the emission layer 150:

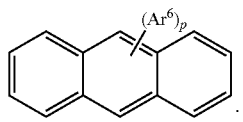

Formula 5

In the above Formula 5, each $Ar^6$ may independently be selected from hydrogen, deuterium, a substituted or unsubstituted alkyl group having 1 to 50 carbon atoms, a substituted or unsubstituted cycloalkyl group having 3 to 50 carbon atoms for forming a ring, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms for forming a ring, a substituted or unsubstituted arylthio group having 6 to 50 carbon atoms for forming a ring, a substituted or unsubstituted alkoxycarbonyl group having 2 to 50 carbon atoms, a substituted or unsubstituted aryl group having 6 to 50 carbon atoms for forming a ring, a substituted or unsubstituted heteroaryl group having 5 to 50 carbon atoms for forming a ring, a substituted or unsubstituted silyl group, a carboxyl group, a halogen atom, a cyano group, a nitro group or a hydroxyl group, and p is an integer selected from 1 to 10.

In Formula 5, each $Ar^6$ may independently include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzoxazolyl group, a pyrazolyl group, a dibenzofuranyl group, a dibenzothienyl group, etc. In one or more embodiments, the phenyl group, the biphenyl group, the terphenyl group, the fluorenyl group, the carbazolyl group, the dibenzofuranyl group, etc. may be used.

The compound represented by Formula 5 may be further represented by a compound selected from the following compounds of a-1 to a-12 (collectively denoted as Formula 6). However, the compound represented by Formula 5 is not limited to the following compounds:

Formula 6

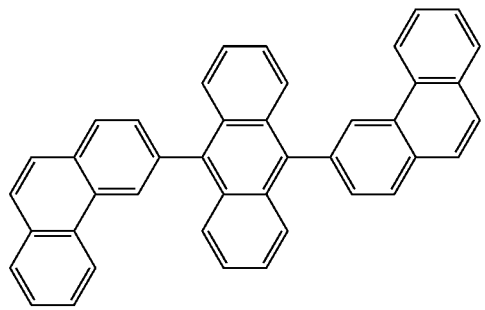

a-1

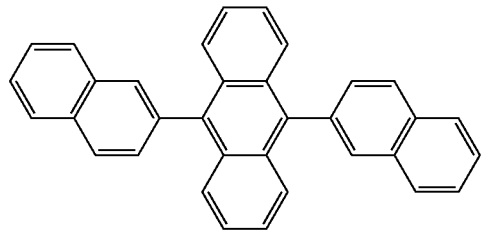

a-2

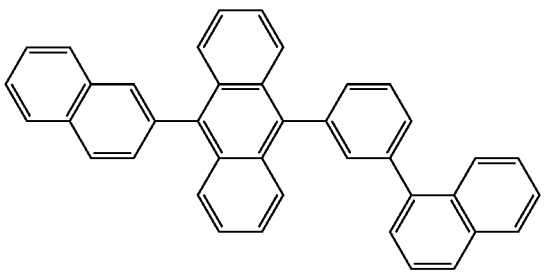

a-3

-continued a-4
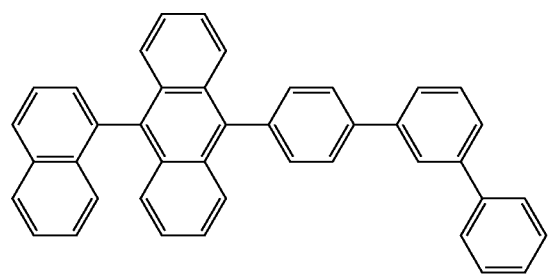

a-5
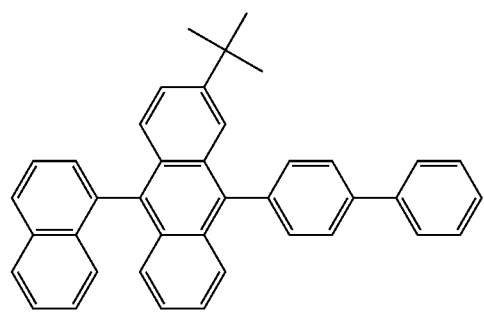

a-6
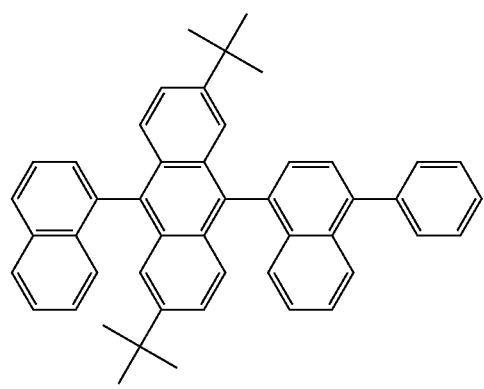

a-7
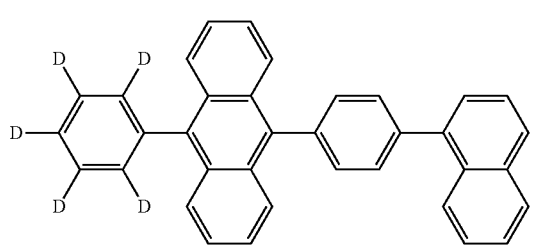

a-8
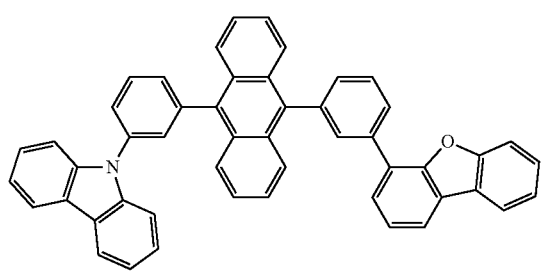

-continued a-9
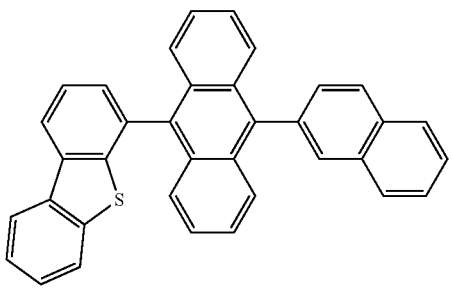

a-10
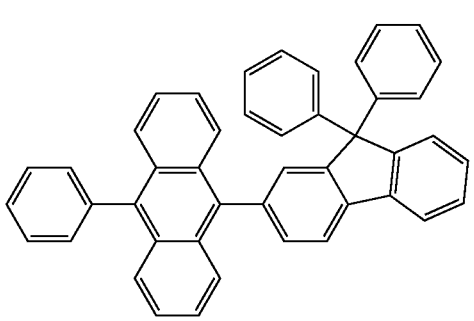

a-11
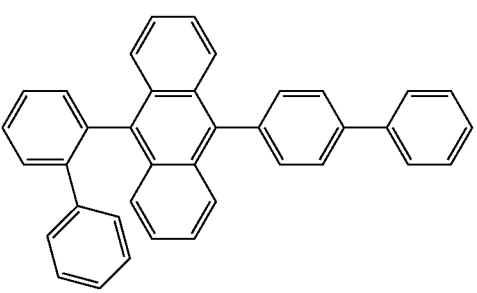

a-12
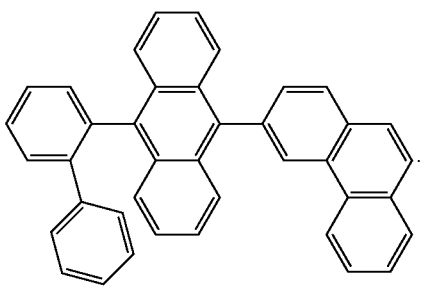

The emission layer 150 may include a dopant such as a styryl derivative (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalene-2-yl)vinyl)phenyl)-N-phenylbenzeneamine (N-BDAVBi)), perylene and derivatives thereof (for example, 2,5,8,11-tetra-t-butylperylene (TBPe)), pyrene and derivatives thereof (for example, 1,1-dipyrene, 1,4-dipyrenylbenzene and 1,4-bis(N, N-diphenylamino)pyrene), etc. However, the kind (e.g., type) of dopant used in embodiments of the present disclosure is not limited thereto.

An electron transport layer 160 including tris(8-hydroxyquinolinato)aluminum (Alq3), a material having a nitrogen-containing aromatic ring (for example, a material including a pyridine ring such as 1,3,5-tri[(3-pyridyl)-phen-3-yl]benzene, a material including a triazine ring such as 2,4,6-tris (3'-(pyridin-3-yl)biphenyl-3-yl)-1,3,5-triazine, and/or a material including an imidazole derivative such as 2-(4-(N-phenylbenzoimidazolyl-1-ylphenyl)-9,10-dinaphthylanthracene) may be formed on the emission layer 150. The electron transport layer 160 may include an electron transport material with electron transporting function and may be formed on the emission layer 150 to a thickness of about 15 nm to about 50 nm. In one or more embodiments, the electron injection layer 170 may be formed on the electron transport layer 160 using a material including lithium fluoride (LiF), lithium-8-quinolinato (Liq), etc. The electron injection layer 170 may facilitate easy injection of electrons from the second electrode 180 and may be formed to a thickness of about 0.3 nm to about 9 nm.

The second electrode 180 may be formed on the electron injection layer 170. In one or more embodiments, the second electrode 180 may be a cathode. In one or more embodiments, the second electrode 180 may be formed as a reflection type (e.g., reflection) electrode using a metal, an alloy, a conductive compound, etc. having a low work function. The second electrode 180 may be formed using, for example, lithium (Li), magnesium (Mg), aluminum (Al), aluminum-lithium (Al—Li), calcium (Ca), magnesium-indium (Mg—In), magnesium-silver (Mg—Ag), etc. In some embodiments, the second electrode 180 may be formed as a transmission type (e.g., transmission) electrode using ITO, IZO, etc. Each of the above-mentioned layers may be formed via an appropriate or suitable layer forming method such as a vacuum evaporation method, a sputtering method, etc., depending on the materials used.

The structure of the organic electroluminescent device 100 according to an embodiment of the present disclosure was described above. The organic electroluminescent device 100 including the material for an organic electroluminescent device according to an embodiment of the present disclosure may have improved emission efficiency.

The structure of the organic electroluminescent device 100 according to an embodiment of the present disclosure is not limited to the above-described embodiments. The organic electroluminescent device 100 may be formed to have a structure similar to that of other known or suitable organic electroluminescent devices. For example, the organic electroluminescent device 100 may omit one or more layers selected from the hole injection layer 130, the electron transport layer 160 and the electron injection layer 170. Each layer of the organic electroluminescent device 100 may be formed as a single layer or a plurality of layers.

The organic electroluminescent device 100 may include a hole blocking layer between the hole transport layer 140 and the emission layer 150 to prevent or reduce the diffusion of triplet excitons or holes into the electron transport layer 160. In some embodiments, the hole blocking layer may be formed using, for example, an oxadiazole derivative, a triazole derivative and/or a phenanthroline derivative.

EXAMPLES

Hereinafter, the organic electroluminescent device according to one or more embodiments of the present disclosure will be explained in more detail by referring to examples and comparative examples. However, the following examples are only for illustration of the organic electroluminescent device according to the present disclosure, and the organic electroluminescent device according to embodiments of the present disclosure is not limited thereto.

Synthetic Example 1: Synthesis of Example Compound 1

Example Compound 1 was synthesized via the following synthetic scheme:

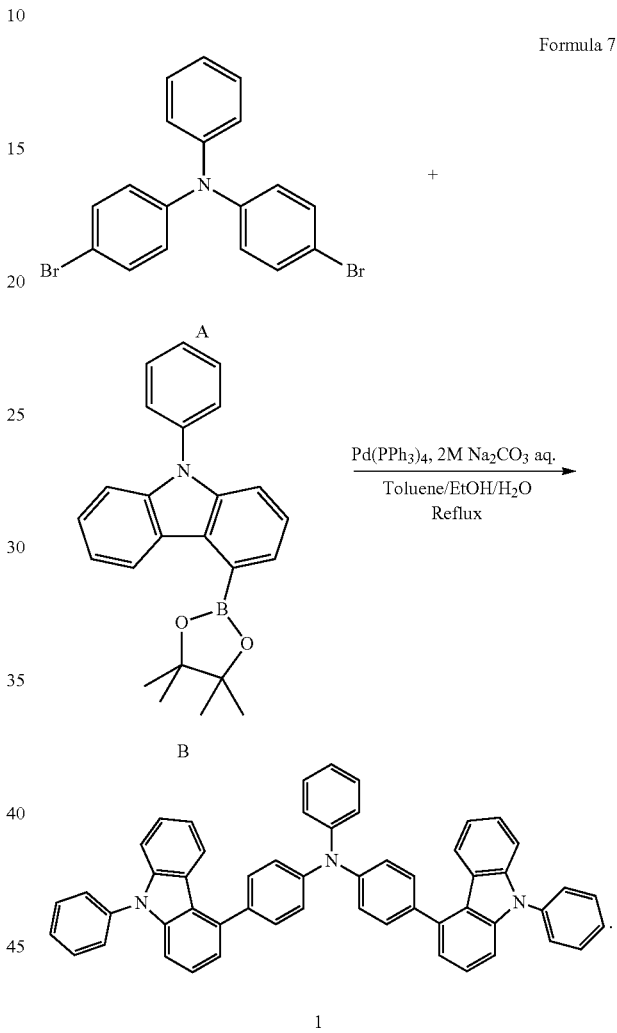

150 g (3.72 mmol) of Compound A, 3.02 g (8.19 mmol) of Compound B, 15 mL of toluene, 7.5 mL of ethanol, and 3.7 mL of a 2 M aqueous solution of sodium carbonate were added to a reaction vessel, and the inner atmosphere of the vessel was replaced with argon. 0.26 g (0.22 mmol) of Pd(PPh$_3$)$_4$ was added thereto, followed by stirring under reflux for about 1.5 hours. After cooling, an organic layer was extracted, dried with anhydrous magnesium sulfate, and filtered, and the filtrate was concentrated using a rotary evaporator. The crude product thus obtained was separated by silica gel column chromatography (developing solution: toluene/hexane), and the solid thus obtained was recrystallized from toluene/hexane to produce 2.17 g (Yield 80%) of Example Compound 1 as a solid white powder. The molecular weight of Example Compound 1 was measured by Fast Atom Bombardment-Mass Spectrometry (FAB-MS), and a value of 727.30 ($C_{54}H_{37}N_3$) was obtained. The chemical shift values of Example Compound 1 measured by ¹H-NMR (300 MHz, CDCl₃) were 7.77 (d, J=8 Hz, 2H), 7.66-7.57 (m, 12H), 7.53-7.47 (m, 2H), 7.42-7.35 (m, 16H), 7.22-7.20 (m, 2H), 7.13-7.10 (m, 3H).

Synthetic Example 2: Synthesis of Example Compound 8

Example Compound 8 was synthesized via the following synthetic scheme:

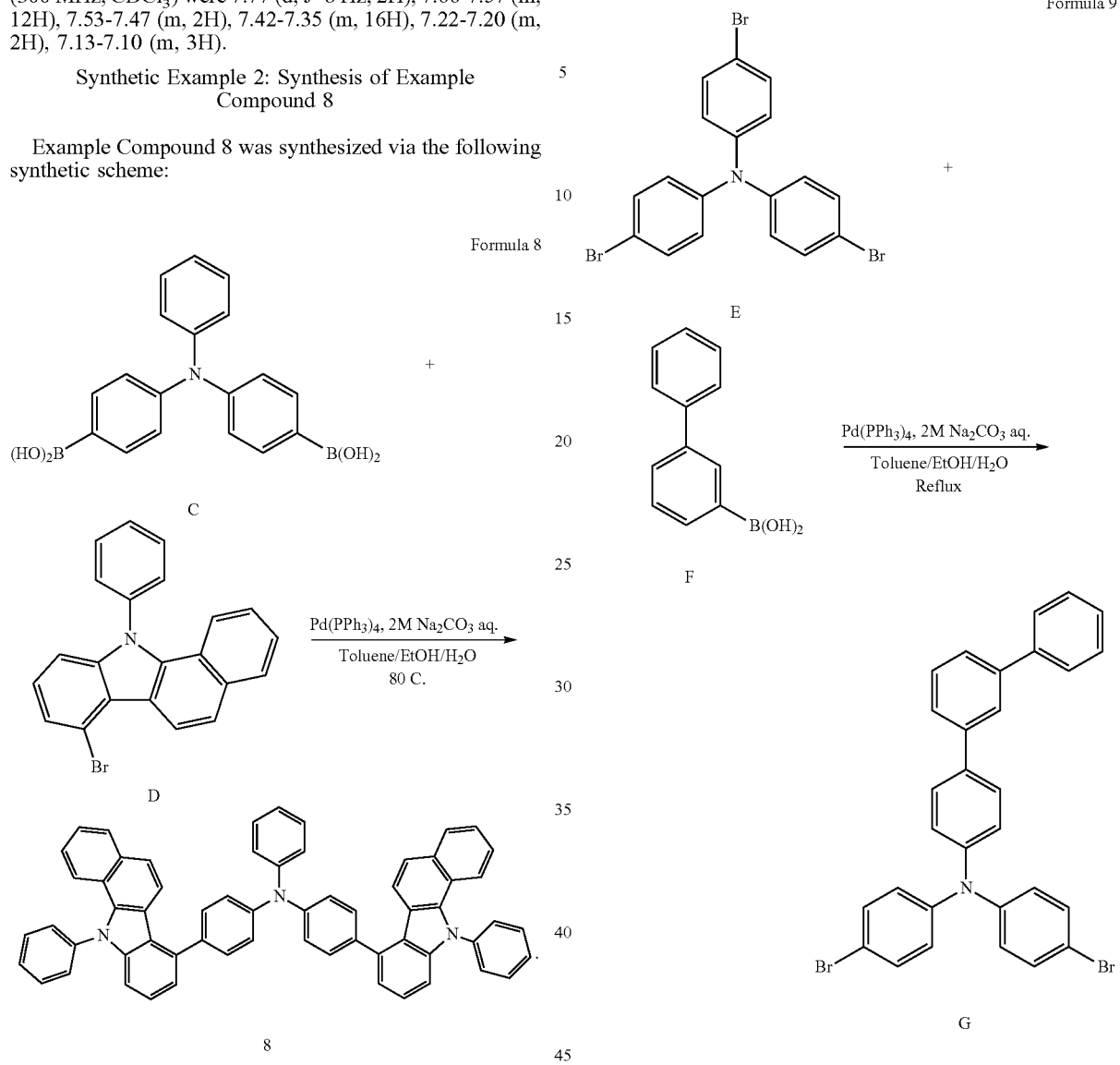

1.00 g (3.00 mmol) of Compound C, 2.68 g (7.21 mmol) of Compound D, 12 mL of toluene, 6.0 mL of ethanol, and 3.0 mL of a 2 M aqueous solution of sodium carbonate were added to a reaction vessel, and the inner atmosphere of the vessel was replaced with argon. 0.21 g (0.18 mmol) of Pd(PPh₃)₄ was added thereto, followed by stirring under reflux for about 1.5 hours. After cooling, an organic layer was extracted, dried with anhydrous magnesium sulfate, and filtered, and the filtrate was concentrated using a rotary evaporator. The crude product thus obtained was separated by silica gel column chromatography (developing solution: toluene/hexane), and the solid thus obtained was recrystallized from toluene/hexane to produce 2.50 g (Yield 90%) of Example Compound 8 as a solid white powder. The molecular weight of Example Compound 8 was measured by FAB-MS, and a value of 828.01 ($C_{62}H_{41}N_3$) was obtained.

Synthetic Example 3: Synthesis of Example Compound 18

Example Compound 18 was synthesized via the following synthetic scheme:

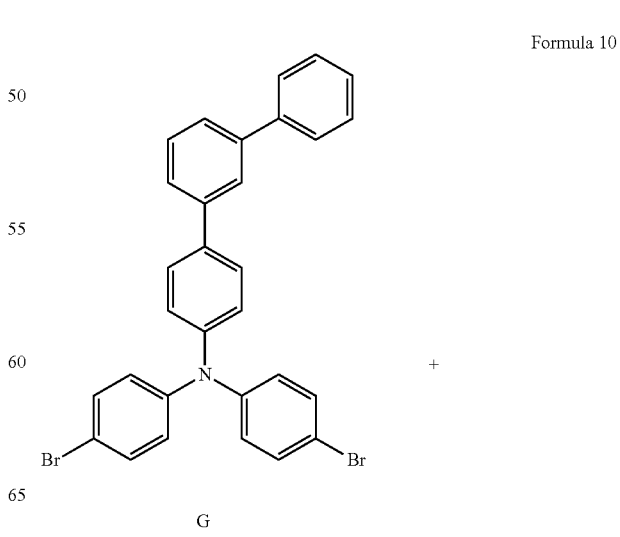

-continued

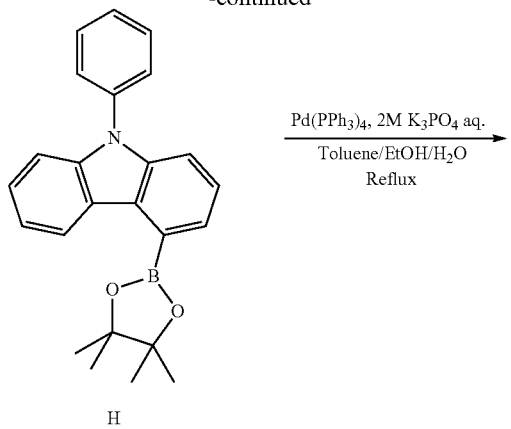

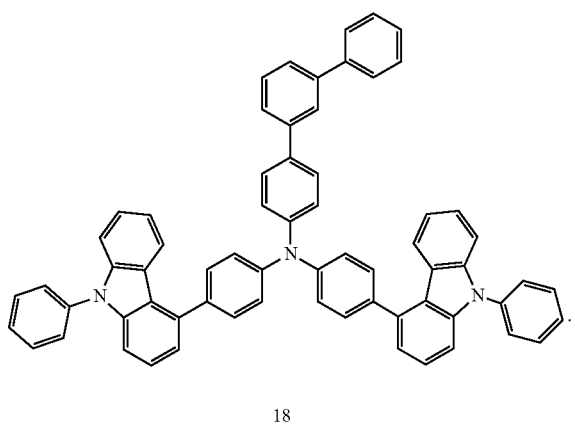

18

Synthesis of Compound G 3.00 g (6.27 mmol) of Compound E, 1.24 g (6.27 mmol) of Compound F, 25 mL of toluene, 12.5 mL of ethanol, and 6.3 mL of a 2 M aqueous solution of sodium carbonate were added to a reaction vessel, and the inner atmosphere of the vessel was replaced with argon. 0.43 g (0.38 mmol) of Pd(PPh$_3$)$_4$ was added thereto, followed by stirring under reflux for about 1.5 hours. After cooling, an organic layer was extracted, dried with anhydrous magnesium sulfate, and filtered, and the filtrate was concentrated using a rotary evaporator. The crude product thus obtained was separated by silica gel column chromatography (developing solution: toluene/hexane) to produce 2.94 g (Yield 85%) of Compound G as a solid white powder. The molecular weight of Compound G was measured by FAB-MS, and a value of 553.00 (C$_{30}$H$_{21}$Br$_2$N) was obtained.

2.50 g (4.50 mmol) of Compound G, 4.00 g (10.8 mmol) of Compound H, 18 mL of toluene, 9.0 mL of ethanol, and 4.5 mL of a 2 M aqueous solution of tripotassium phosphate were added to a reaction vessel, and the inner atmosphere of the vessel was replaced with argon. 0.31 g (0.27 mmol) of Pd(PPh$_3$)$_4$ was added thereto, followed by stirring under reflux for about 1.5 hours. After air cooling, an organic layer was extracted, dried with anhydrous magnesium sulfate, and filtered, and the filtrate was concentrated using a rotary evaporator. The crude product thus obtained was separated by silica gel column chromatography (developing solution: toluene/hexane) to produce 3.64 g (Yield 92%) of Example Compound 18 as a solid white powder. The molecular weight of Example Compound 18 was measured by FAB-MS, and a value of 879.36 (C$_{66}$H$_{45}$N$_3$) was obtained.

Manufacture of Organic Electroluminescent Device

The organic electroluminescent devices were manufactured using the following method. First, an ITO-glass substrate was patterned and washed in advance, then subjected to surface treatment using UV-ozone (O$_3$). The thickness of the ITO layer (the first electrode) was about 150 nm. After ozone treatment, the substrate was washed. The washed substrate was placed in a glass bell jar evaporator for forming an organic layer, and a hole injection layer (HIL), a hole transport layer (HTL), an emission layer, and an electron transport layer (ETL) were evaporated one by one under a vacuum degree of about 10$^{-4}$ to about 10$^{-5}$ Pa. The material of the hole injection layer (HIL) was 2-TNATA, and the thickness thereof was about 60 nm. The materials of the HTL are shown in Table 1, and the thickness thereof was about 30 nm.

The thickness of the emission layer was about 25 nm. The host (e.g., emission material) was 9,10-di(2-naphthyl)anthracene (ADN). The dopant was 2,5,8,11-tetra-I-butylperylene (TBP). The amount of the dopant was about 3 wt % on the basis of the amount of the host. The material of the electron transport layer was Alq3, and the thickness thereof was about 25 nm. Subsequently, the substrate was transferred to a glass bell jar evaporator for forming a metal layer, and the electron injection layer (EIL) and a cathode material were evaporated under a vacuum degree of about 10$^{-4}$ to about 10$^{-5}$ Pa. The material of the electron injection layer was LiF, and the thickness thereof was about 1.0 nm. The material of the second electrode was Al, and the thickness thereof was about 100 nm.

TABLE 1

| Manufactured device | HTL material | Current density (mA/cm$^2$) | Voltage (V) | Emission efficiency (cd/A) |
|---|---|---|---|---|
| Example 1 | Example Compound 1 | 10 | 6.3 | 7.3 |
| Example 2 | Example Compound 8 | 10 | 6.5 | 7.1 |
| Example 3 | Example Compound 18 | 10 | 6.3 | 7.0 |
| Comparative Example 1 | Comparative Compound C1 | 10 | 6.4 | 6.3 |
| Comparative Example 2 | Comparative Compound C2 | 10 | 7.6 | 5.5 |
| Comparative Example 3 | Comparative Compound C3 | 10 | 6.6 | 6.6 |

In Table 1, Comparative Compounds C1, C2 and C3 may be represented by the following structures. Comparative Compound C1 is an example of an amine derivative including one carbazolyl group. Comparative Compound C2 is an example of a naphthalene derivative including two carbazolyl groups, in which carbon atoms at position 4 of each carbazolyl group are combined with the carbon atoms of naphthalene at positions 1 and 4. Comparative Compound C3 is an example of an amine derivative including two carbazolyl groups, in which the carbon atom of the carbazolyl group at position 3 is combined with the nitrogen atom of an amine.

Formula 11

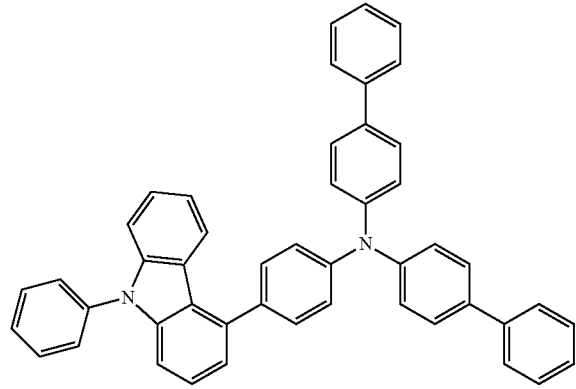

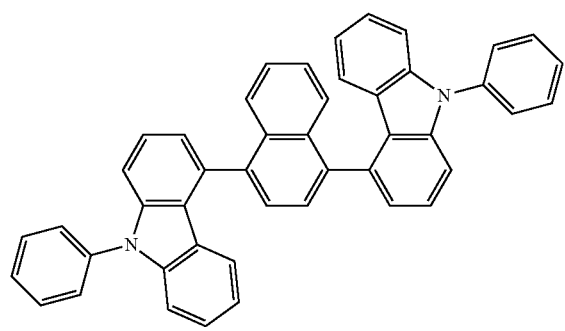

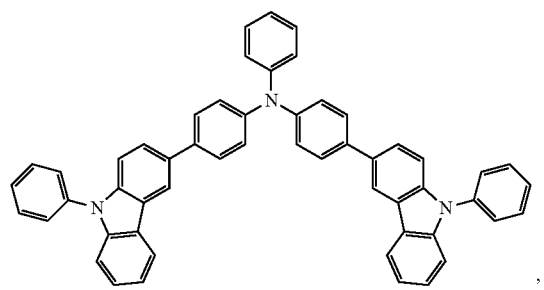

Comparative Compound C1 Comparative Compound C2 Comparative Compound C3.

Evaluation of Properties

The driving voltages and the emission lives of the organic electroluminescent devices thus manufactured were measured. The luminescent properties of the organic electroluminescent devices were evaluated using the brightness light distribution characteristics measurement system (C9920-11) of HAMAMATSU Photonics Co. The current densities were measured at about 10 mA/cm$^2$. The results are shown in Table 1.

Referring to Table 1, the organic electroluminescent devices of Examples 1 to 3, in which a hole transport layer (HTL) was formed using the amine derivative according to example embodiments, have improved emission efficiencies when compared to the organic electroluminescent devices of Comparative Examples 1 to 3.

The organic electroluminescent devices of Examples 1 to 3, in which the HTL was formed using the amine derivative according to example embodiments, have improved emission efficiencies when compared Comparative Example 1. The amine derivative used in Comparative Example 1 does not have a symmetric molecular structure around its nitrogen atom. The organic electroluminescent devices of Examples 1 to 3, in which the HTL was formed using an monoamine derivative according to example embodiments, have improved emission efficiencies when compared to Comparative Example 2, in which a naphthalene derivative having two carbazolyl groups was used.

Examples 1 to 3 and Comparative Example 3 will be compared. In Example Compounds 1, 8 and 18, the carbon atoms of each carbazolyl group at position 4 are combined (e.g., coupled) with the nitrogen atom of an amine via a phenylene group. In Comparative Compound C3, the carbon atoms of each carbazolyl group at position 3 are combined with the nitrogen atom of an amine via a phenylene group. The difference in molecular structures may be associated with larger or increased emission efficiencies for Examples 1 to 3 compared to Comparative Example 3.

As shown in the following structure (3-1), in Example Compounds 1, 8 and 18, when the carbon atom of the carbazolyl group at position 4 is combined (e.g., coupled) with the nitrogen atom of the amine via the phenylene group, steric repulsion may generate torsion between the carbazolyl group and the phenylene group. Since π electron conjugation is resultantly decreased, the triplet energy level (T1) may be increased, and the molecule may have increased utility as an electron barrier in the hole transport layer. Therefore, electrons may be confined (e.g., confined to the emission layer), and the emission efficiency of an organic electroluminescent device may be improved or increased.

As shown in the following structure (3-2), in Comparative Compound C3, when the carbon atom of the carbazolyl group at position 3 (or position 2) is combined (e.g., coupled) with the nitrogen atom of the amine via the phenylene group, the lesser degree of steric repulsion may not generate, or may generate comparatively less torsion between the carbazolyl group and the phenylene group. When torsion is not generated enough in Comparative Compound C3, π electron conjugation is not substantially decreased, and the triplet energy level is not increased when compared to Example Compounds 1, 8 and 18. The difference in triplet energy levels caused by the difference in molecular structure is associated with an increase in the emission efficiencies of Examples 1 to 3 compared to that of Comparative Example 3. The triplet energy level of Comparative Compound C1 (in which the carbon atom of one carbazolyl group at position 4 is combined or coupled with the nitrogen atom of the amine) is about 2.32 eV, while the triplet energy level of Comparative Compound C3 (in which the carbon atom of the carbazolyl group at position 3 is combined or coupled with the nitrogen atom of the amine is about 2.24 eV. The triplet energy level of a compound in which the carbon atom of the carbazolyl group at position 2 is combined or coupled with the nitrogen atom of the amine) is about 2.13 eV. When the carbon atom of the carbazolyl group at position 4 is coupled (e.g., combined) with the nitrogen atom of the amine, a higher energy level value may be obtained relative to the analogous molecules in which the carbon atom of the carbazolyl group at position 3 or position 2 is coupled to the nitrogen atom of the amine.

Formula 12

Structure (3-1),

Structure (3-2)

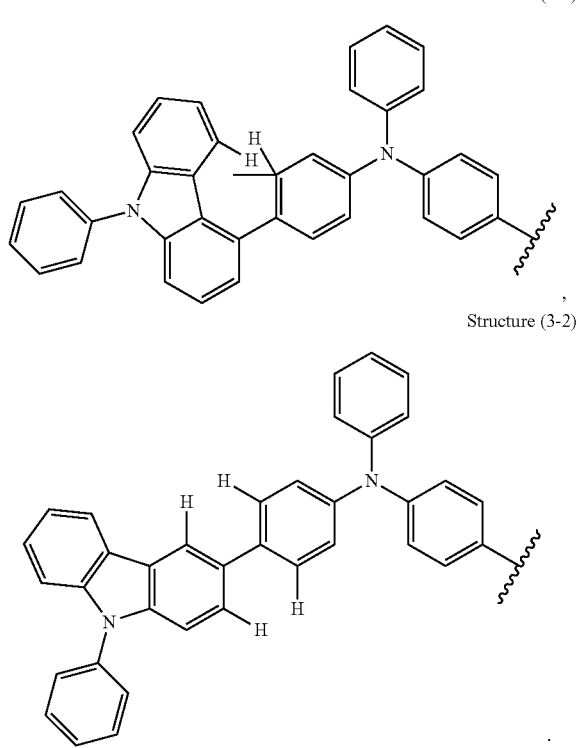

As described above, the emission efficiency of an organic electroluminescent device may be largely improved in the blue to bluish green region of example embodiments.

According to an embodiment of the present disclosure, when the material for an organic electroluminescent device includes an amine derivative represented by Formula 1, the organic electroluminescent device including the same may have a largely improved or increased emission efficiency. Therefore, the material for an organic electroluminescent device according to example embodiments may be beneficial in one or more practical uses.

As described above, the emission efficiency of an organic electroluminescent device may be improved according to the present disclosure.

As used herein, expressions such as "at least one of" and "one of", when preceding a list of elements, modify the entire list of elements and do not modify the individual elements of the list. Further, the use of "may" when describing embodiments of the present disclosure refers to "one or more embodiments of the present disclosure".

As used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

The above-disclosed subject matter is to be considered illustrative and not restrictive, and the appended claims and equivalents thereof are intended to cover all such modifications, enhancements, and other embodiments, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A material for an organic electroluminescent device comprising an amine derivative represented by Formula 1:

Formula 1

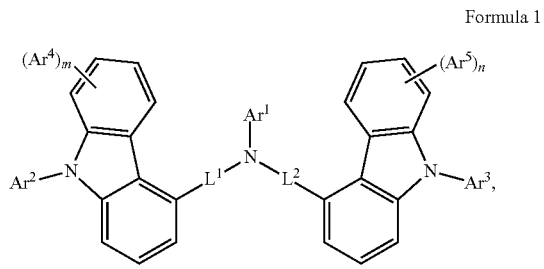

wherein $Ar^1$ to $Ar^3$ are each independently selected from a substituted or unsubstituted aryl group having 6 to 50 carbon atoms for forming a ring, a substituted and unsubstituted heteroaryl group having 5 to 50 carbon atoms for forming a ring, $Ar^4$ and $Ar^5$ are each independently selected from hydrogen, deuterium, a halogen atom, a substituted or unsubstituted alkyl group having 1 to 20 carbon atoms, a substituted or unsubstituted aryl group having 6 to 50 carbon atoms for forming a ring, a substituted or unsubstituted heteroaryl group having 5 to 50 carbon atoms for forming a ring, and an aryl group or a heteroaryl group formed via cyclocondensation of adjacent optional substituents, $L^1$ and $L^2$ are each independently selected from a substituted or unsubstituted arylene group having 6 to 18 carbon atoms for forming a ring, and a substituted or unsubstituted heteroarylene group having 5 to 15 carbon atoms for forming a ring, and n and m are each independently an integer selected from 0 to 4.

2. The material for an organic electroluminescent device of claim 1, wherein $Ar^1$ to $Ar^3$ are each independently selected from a substituted or unsubstituted aryl group having 6 to 18 carbon atoms for forming a ring, and a substituted or unsubstituted heteroaryl group having 5 to 18 carbon atoms for forming a ring.

3. The material for an organic electroluminescent device of claim 2, wherein $Ar^1$ to $Ar^3$ are each independently selected from a substituted or unsubstituted phenyl group and a substituted or unsubstituted biphenyl group.

4. The material for an organic electroluminescent device of claim 1, wherein $L^1$ and $L^2$ are a phenylene group.

5. The material for an organic electroluminescent device of claim 1, wherein $Ar^1$ to $Ar^3$ are each independently selected from a substituted or unsubstituted phenyl group, a substituted or unsubstituted biphenyl group, a substituted or unsubstituted terphenyl group, a substituted or unsubstituted naphthyl group, a substituted or unsubstituted anthryl group, a substituted or unsubstituted phenanthrenyl group, a substituted or unsubstituted fluorenyl group, a substituted or unsubstituted indenyl group, a substituted or unsubstituted pyrenyl group, a substituted or unsubstituted fluoranthenyl group, a substituted or unsubstituted triphenylenyl group, a substituted or unsubstituted perylenyl group, a substituted or unsubstituted naphthylphenyl group, and a substituted or unsubstituted biphenylenyl group.

6. The material for an organic electroluminescent device of claim 1, wherein $Ar^1$ to $Ar^3$ are each independently selected from a substituted or unsubstituted pyridyl group, a substituted or unsubstituted quinolyl group, a substituted or unsubstituted isoquinolyl group, a substituted or unsubstituted indolyl group, a substituted or unsubstituted benzoxazolyl group, a substituted or unsubstituted benzothiazolyl group, a substituted or unsubstituted quinoxalyl group, a substituted or unsubstituted benzoimidazolyl group, a substituted or unsubstituted indazolyl group, a substituted or unsubstituted benzofuranyl group, a substituted or unsubstituted isobenzofuranyl group, a substituted or unsubstituted dibenzofuranyl group, a substituted or unsubstituted phenoxazinyl group, a substituted or unsubstituted benzothiophenyl group, and a substituted or unsubstituted dibenzothiophenyl group.

7. The material for an organic electroluminescent device of claim 1, wherein the material for an organic electroluminescent device represented by Formula 1 is selected from compounds 1 to 4 and 6 to 8 of Formula 2:

Formula 2

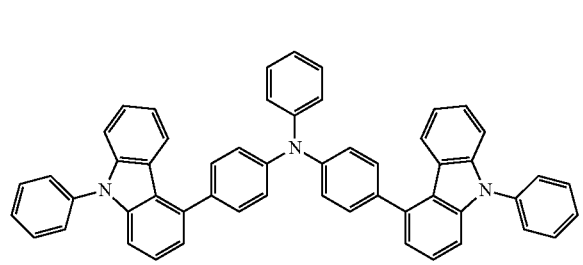

1

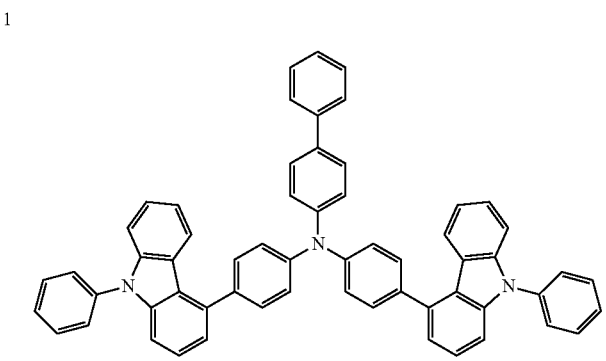

2

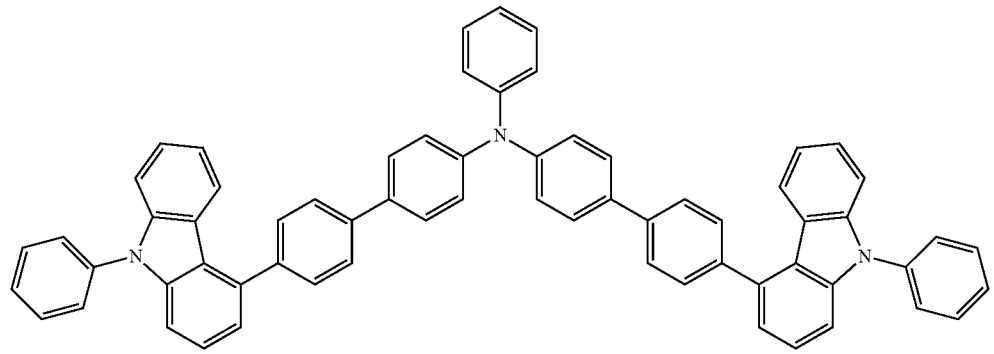

3

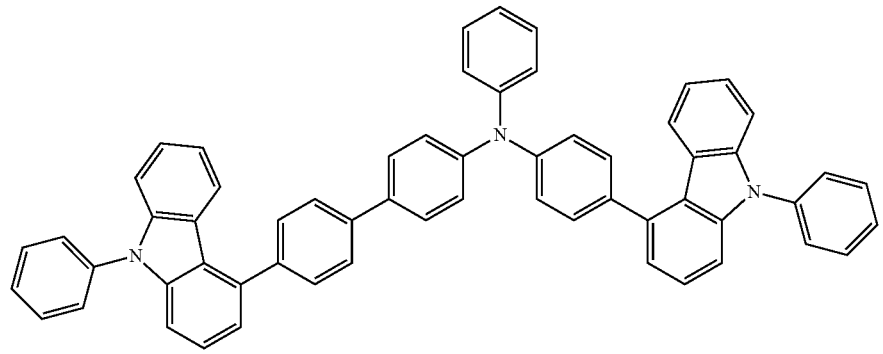

4

-continued
6
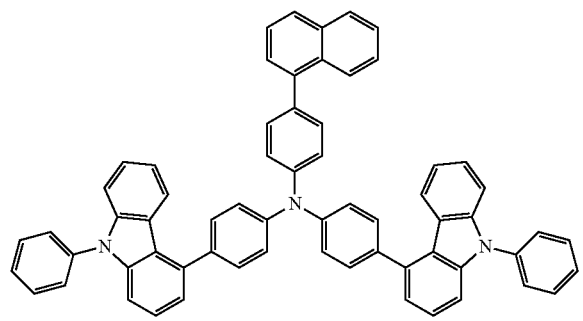
7
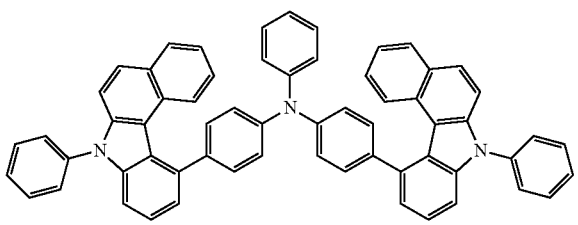
8
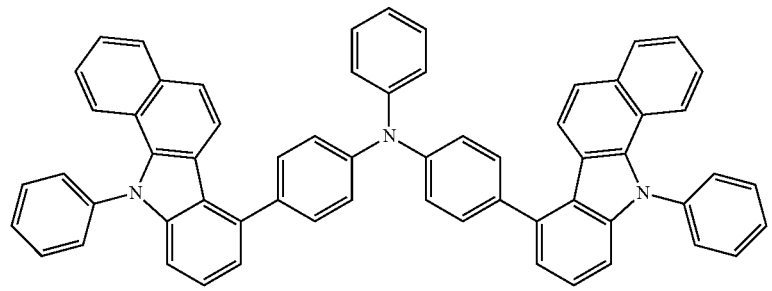
8. The material for an organic electroluminescent device of claim 1, wherein the material for an organic electroluminescent device represented by Formula 1 is selected from compounds 9 to 16 of Formula 3:
Formula 3
9
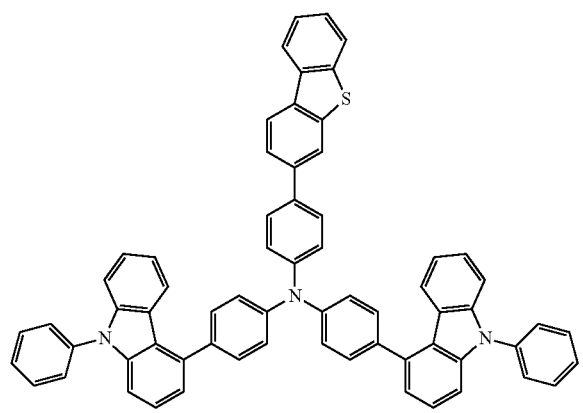
10
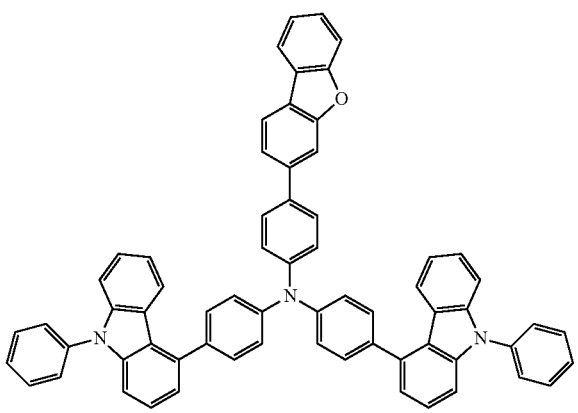
11
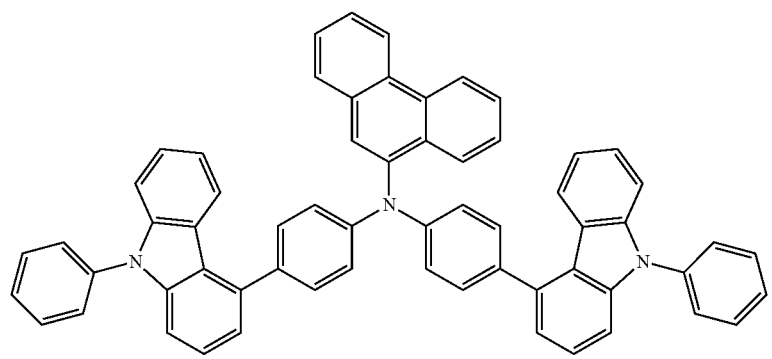

-continued

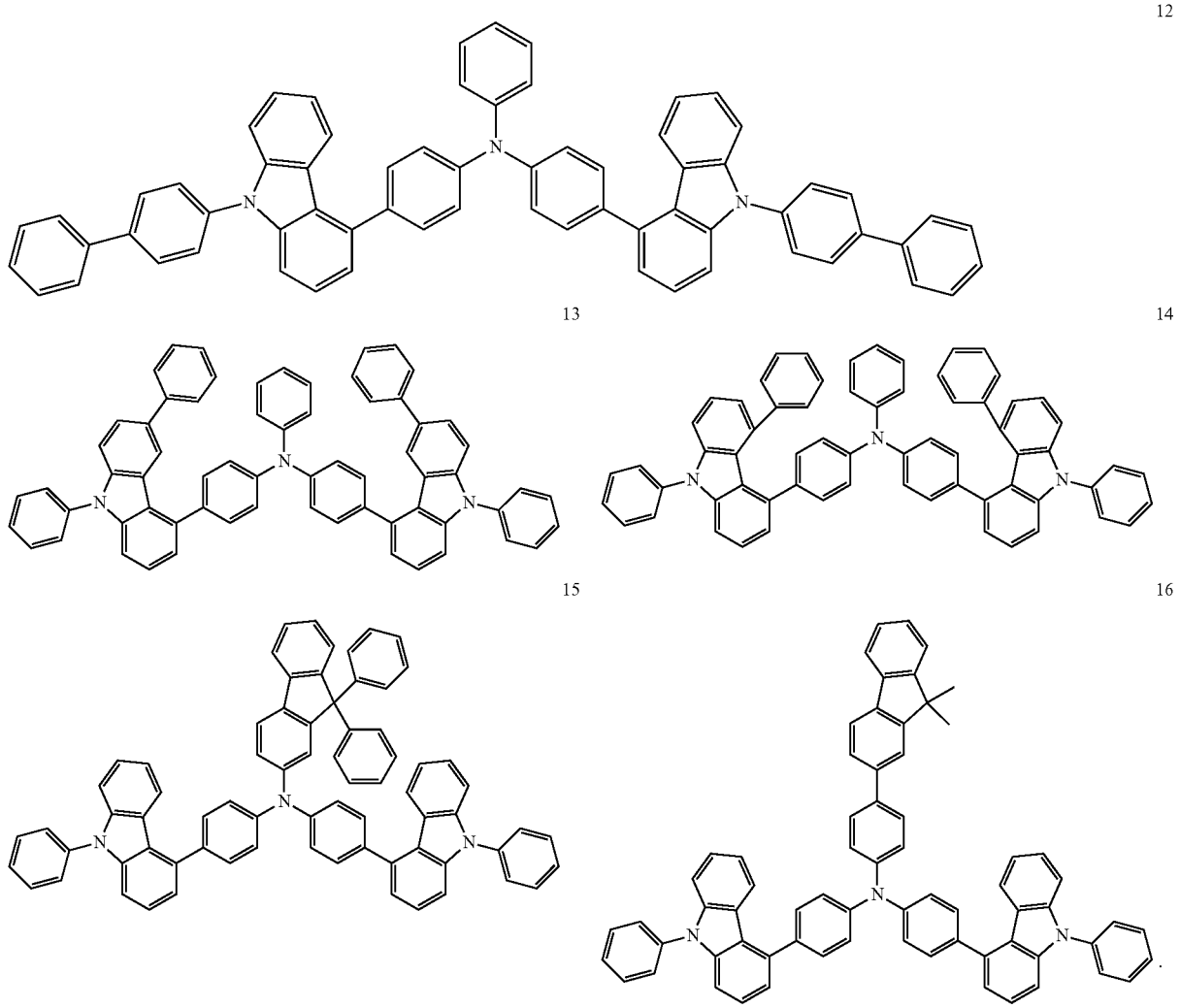

9. The material for an organic electroluminescent device of claim 1, wherein the material for an organic electroluminescent device represented by Formula 1 is selected from compounds 17 to 18 of Formula 4:

Formula 4

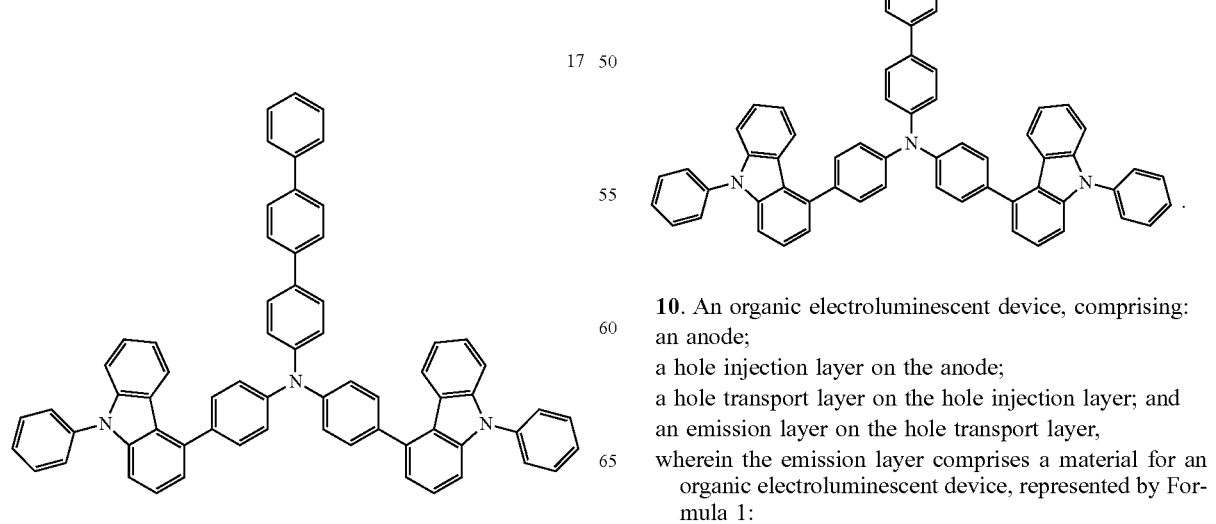

10. An organic electroluminescent device, comprising:
an anode;
a hole injection layer on the anode;
a hole transport layer on the hole injection layer; and
an emission layer on the hole transport layer,
wherein the emission layer comprises a material for an organic electroluminescent device, represented by Formula 1:

Formula 1

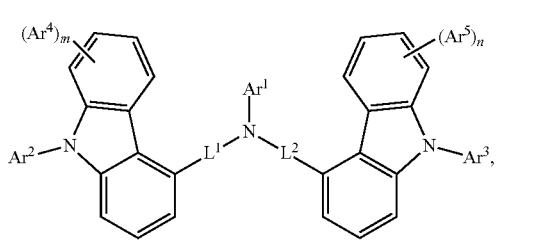

wherein Ar¹ to Ar³ are each independently selected from a substituted or unsubstituted aryl group having 6 to 50 carbon atoms for forming a ring, and a substituted or unsubstituted heteroaryl group having 5 to 50 carbon atoms for forming a ring, Ar⁴ and Ar^y are each independently selected from hydrogen, deuterium, a halogen atom, a substituted or unsubstituted alkyl group having 1 to 20 carbon atoms, a substituted or unsubstituted aryl group having 6 to 50 carbon atoms for forming a ring, a substituted or unsubstituted heteroaryl group having 5 to 50 carbon atoms for forming a ring, and an aryl group or a heteroaryl group formed via cyclocondensation of adjacent optional substituents, L¹ and L² are each independently selected from a substituted or unsubstituted arylene group having 6 to 18 carbon atoms for forming a ring, and a substituted or unsubstituted heteroarylene group having 5 to 15 carbon atoms for forming a ring, and n and m are each independently an integer selected from 0 to 4.

11. The organic electroluminescent device of claim 10, wherein at least one layer selected from the hole injection layer and the hole transport layer comprises the material for an organic electroluminescent device represented by Formula 1.

12. The organic electroluminescent device of claim 10, wherein Ar¹ to Ar³ are each independently selected from a substituted or unsubstituted aryl group having 6 to 18 carbon atoms for forming a ring, and a substituted or unsubstituted heteroaryl group having 5 to 18 carbon atoms for forming a ring.

13. The organic electroluminescent device of claim 12, wherein Ar¹ to Ar³ are each independently selected from a substituted or unsubstituted phenyl group and a substituted or unsubstituted biphenyl group.

14. The organic electroluminescent device of claim 10, wherein L¹ and L² are a phenylene group.

15. The organic electroluminescent device of claim 10, wherein Ar¹ to Ar³ are each independently selected a substituted or unsubstituted phenyl group, a substituted or unsubstituted biphenyl group, a substituted or unsubstituted terphenyl group, a substituted or unsubstituted naphthyl group, a substituted or unsubstituted anthryl group, a substituted or unsubstituted phenanthrenyl group, a substituted or unsubstituted fluorenyl group, a substituted or unsubstituted indenyl group, a substituted or unsubstituted pyrenyl group, a substituted or unsubstituted fluoranthenyl group, a substituted or unsubstituted triphenylenyl group, a substituted or unsubstituted perylenyl group, a substituted or unsubstituted naphthylphenyl group, and a substituted or unsubstituted biphenylenyl group.

16. The organic electroluminescent device of claim 10, wherein Ar¹ to Ar³ are each independently selected from a substituted or unsubstituted pyridyl group, a substituted or unsubstituted quinolyl group, a substituted or unsubstituted isoquinolyl group, a substituted or unsubstituted indolyl group, a substituted or unsubstituted benzoxazolyl group, a substituted or unsubstituted benzothiazolyl group, a substituted or unsubstituted quinoxalyl group, a substituted or unsubstituted benzoimidazolyl group, a substituted or unsubstituted indazolyl group, a substituted or unsubstituted benzofuranyl group, a substituted or unsubstituted isobenzofuranyl group, a substituted or unsubstituted dibenzofuranyl group, a substituted or unsubstituted phenoxazinyl group, a substituted or unsubstituted benzothiophenyl group, and a substituted or unsubstituted dibenzothiophenyl group.

17. The organic electroluminescent device of claim 10, wherein the material for an organic electroluminescent device represented by Formula 1 is selected from compounds 1 to 4 and 6 to 8 of Formula 2:

Formula 2

1

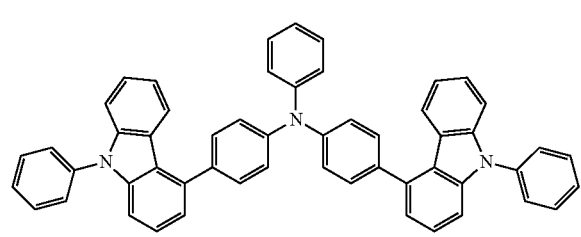

2

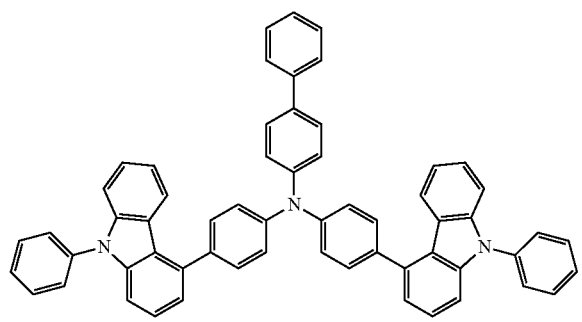

3
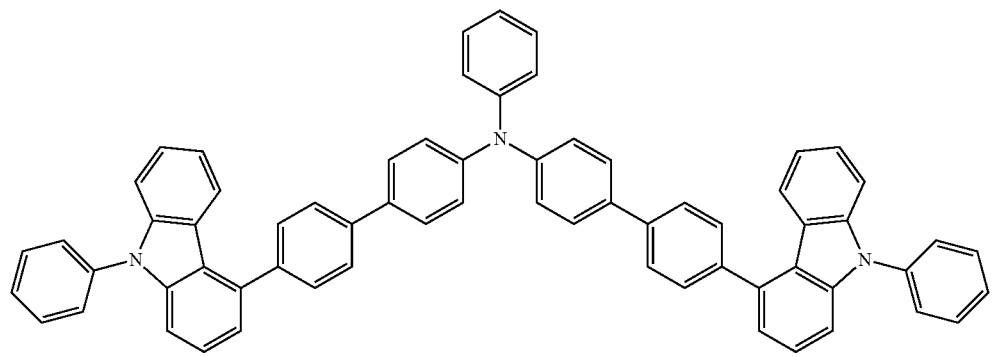
4
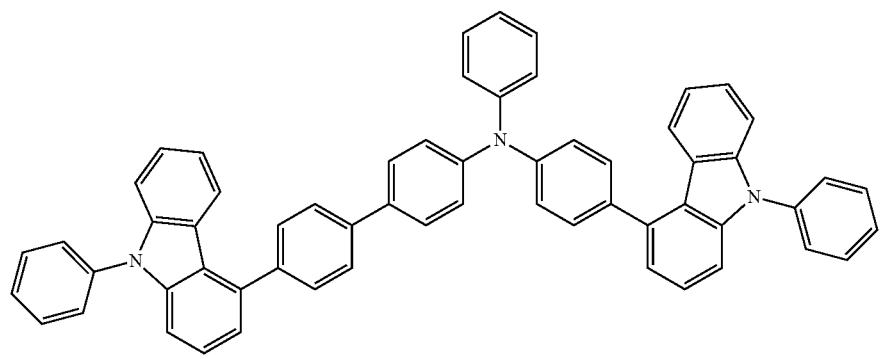
6 7
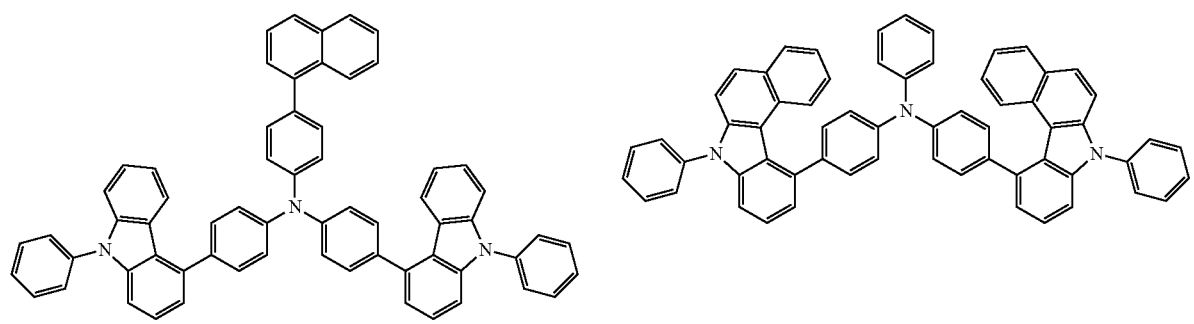
8
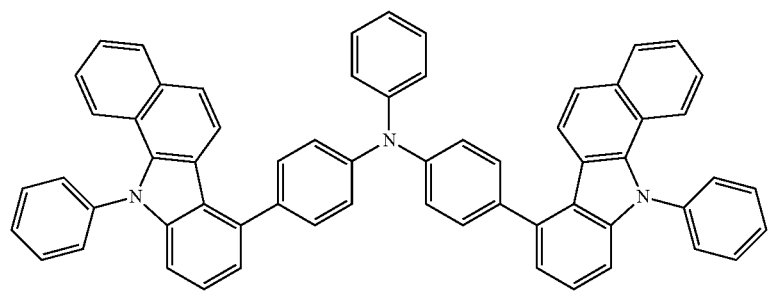
18. The organic electroluminescent device of claim 10, wherein the material for an organic electroluminescent device represented by Formula 1 is selected from compounds 9 to 16 of Formula 3:

Formula 3
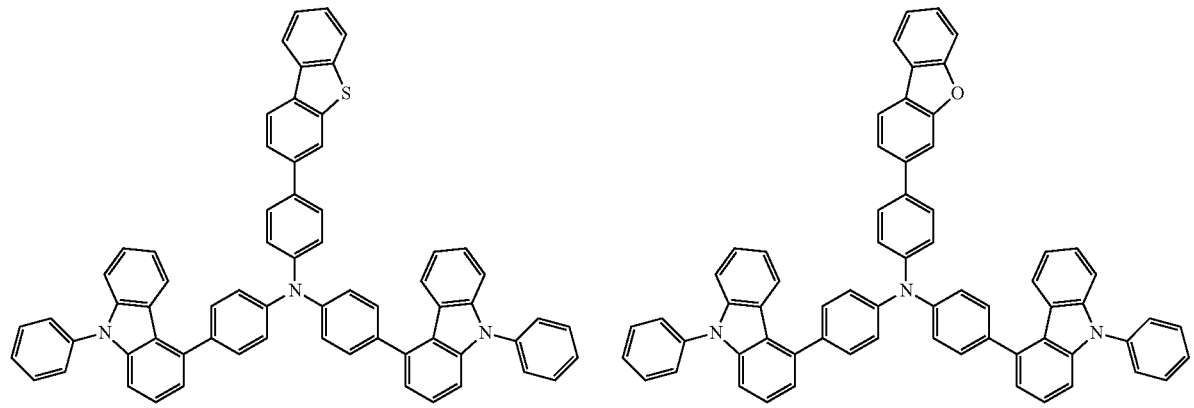
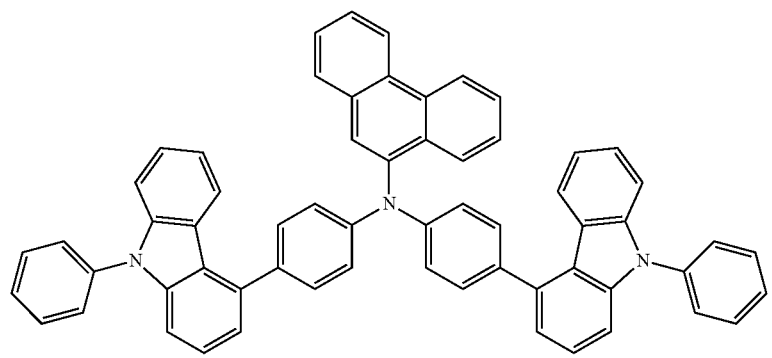
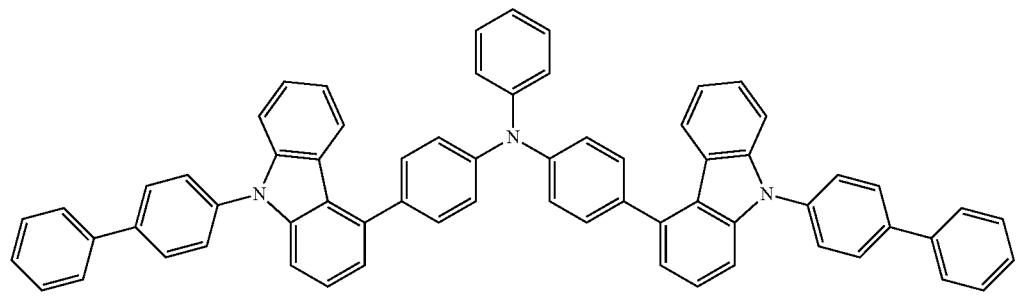
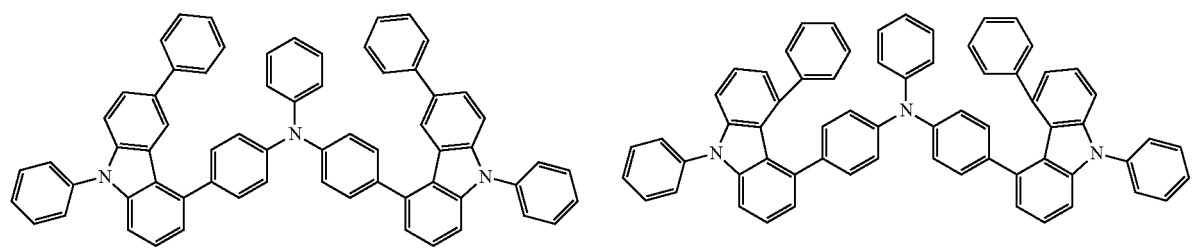

15
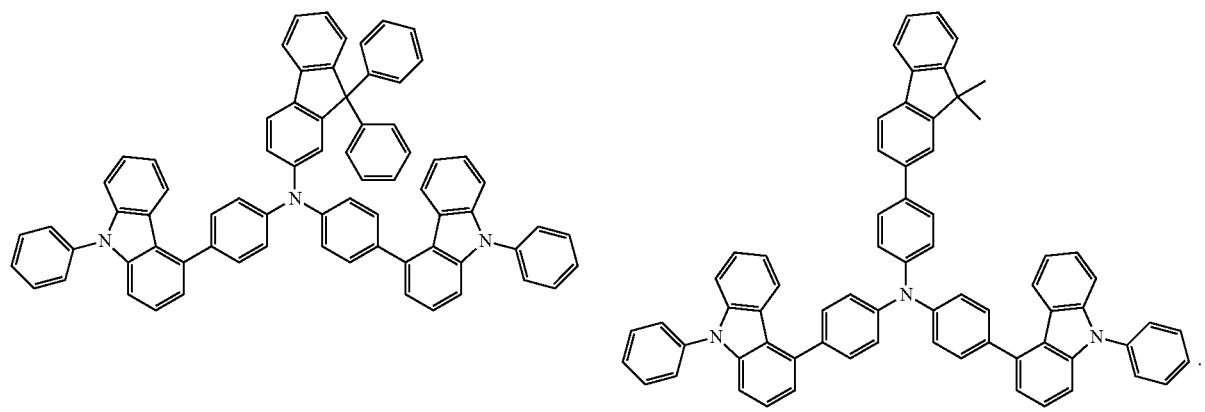
16
19. The organic electroluminescent device of claim 10, wherein the material for an organic electroluminescent device represented by Formula 1 is selected from compounds 17 to 18 of Formula 4:
Formula 4
17
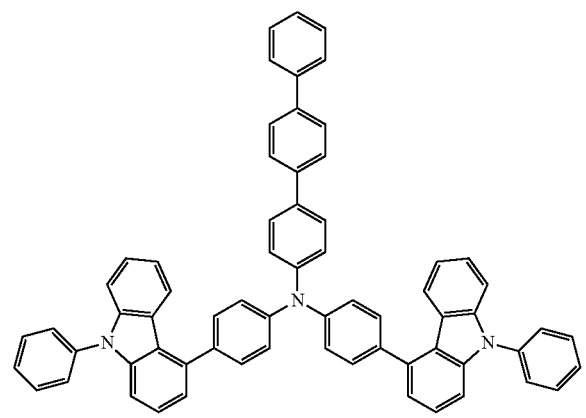
18
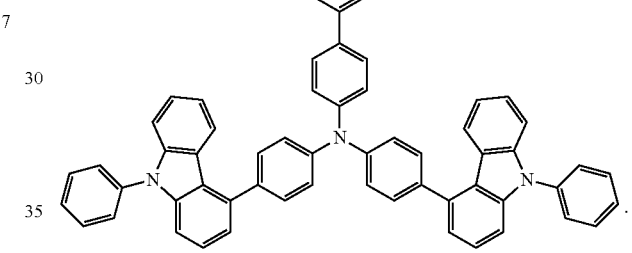
20. The organic electroluminescent device of claim 10, wherein the emission layer comprises a blue luminescent material or a green luminescent material.
* * * * *